United States Patent
Mashita et al.

(10) Patent No.: US 9,291,581 B2
(45) Date of Patent: Mar. 22, 2016

(54) METHOD FOR EVALUATING ENERGY LOSS, CHIPPING RESISTANCE AND ABRASION RESISTANCE OF POLYMERIC MATERIAL

(71) Applicant: SUMITOMO RUBBER INDUSTRIES, LTD., Kobe-shi, Hyogo (JP)

(72) Inventors: Ryo Mashita, Kobe (JP); Hiroyuki Kishimoto, Kobe (JP); Tomomi Masui, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 204 days.

(21) Appl. No.: 14/071,149

(22) Filed: Nov. 4, 2013

(65) Prior Publication Data

US 2014/0140483 A1  May 22, 2014

(30) Foreign Application Priority Data

Nov. 21, 2012 (JP) .................................. 2012-255589

(51) Int. Cl.
  *G01N 23/201* (2006.01)
  *G01N 23/202* (2006.01)

(52) U.S. Cl.
  CPC ............ *G01N 23/202* (2013.01); *G01N 23/201* (2013.01); *G01N 2223/1006* (2013.01); *G01N 2223/106* (2013.01); *G01N 2223/1016* (2013.01); *G01N 2223/623* (2013.01)

(58) Field of Classification Search
  CPC .............. G01N 23/202; G01N 23/201; G01N 2223/1016; G01N 2223/623; G01N 2223/1006; G01N 2223/106
  USPC ....................................... 378/86–88
  See application file for complete search history.

(56) References Cited

U.S. PATENT DOCUMENTS

2008/0013685 A1* 1/2008 Iwasaki et al. ................... 378/86
2009/0250600 A1* 10/2009 Khemliche et al. ........... 250/251

FOREIGN PATENT DOCUMENTS

JP     2004-132869 A    4/2004
JP     2009-46088 A     3/2009

(Continued)

OTHER PUBLICATIONS

Ashdown et al., "Small-Angle Neutron-Scattering Studies on Ordered Polymer Colloid Dispersions", Langmuir, 1990, 6, pp. 303-307.

(Continued)

*Primary Examiner* — Michael Maskell
(74) *Attorney, Agent, or Firm* — Birch, Stewart, Kolasch & Birch, LLP

(57) ABSTRACT

The present invention provides a method for evaluating energy loss in a polymeric material, wherein the method provides sufficient evaluation of the difference in performance between samples with excellent measurement accuracy; a method for evaluating chipping resistance of a polymeric material, wherein the method provides evaluation in a short period of time and at low cost with excellent measurement accuracy; and a method for evaluating abrasion resistance of a polymeric material, wherein the method provides sufficient evaluation of the difference in performance between samples with excellent measurement accuracy. The present invention relates to methods for evaluating energy loss, chipping resistance, and abrasion resistance of a polymeric material, and the methods include irradiating the polymeric material with X-rays or neutrons to perform X-ray scattering measurement or neutron scattering measurement.

15 Claims, 1 Drawing Sheet

(56) References Cited

FOREIGN PATENT DOCUMENTS

JP          2010-181342 A       8/2010
JP          2013-248287 A      12/2013
WO      WO 2013/065405 A1      5/2013

OTHER PUBLICATIONS

Shan et al., "Preparation, Characterization, and Application of NR/SBR/Organoclay Nanocomposites in the Tire Industry", Journal of Applied Polymer Science, vol. 119, 2011, pp. 1185-1194.
Shinohara et al., "Characterization of two-dimensional ultra-small-angle X-ray scattering apparatus for application to rubber filled with spherical silica under elongation", Journal of Applied Crystallography, 2007, 40, pp. s397-s401.
Sonnenschein et al., "Comparison of adipate and succinate polyesters in thermoplastic polyurethanes", Polymer, 51, 2010, pp. 3685-3692.
Udagawa, "Changes in the Fine Structure of Rubber Vulcanizates Fatigued by Repeated Force", Rubber Chemistry and Technology, 1988, 61, pp. 1-13.
Wang et al., "Effect of Epoxidized Natural Rubber on the Properties of Rectorite/Carbon Black/Natural Rubber Nanocomposites", Journal of Applied Polymer Science, 2013, pp. 2578-2584.
Amemiya et al., "Long-term Report 2", Spring-8 Information, vol. 14, No. 2, 2009, pp. 149-153.
Kishimoto, AFMc No. 32, RCTF Preprints, 2008, vol. 32, pp. 35-40.
Shinohara et al., "Small-angle X-ray scattering of filled rubber", Function & Materials, 2007, vol. 27, No. 4, pp. 83-90.
Togashi et al., "Wear of tire, biased wear evaluation, and its improved technology," The Society of Rubber Science and Technology, Japan, vol. 69, No. 11, Nov. 1996, pp. 739-748.

* cited by examiner

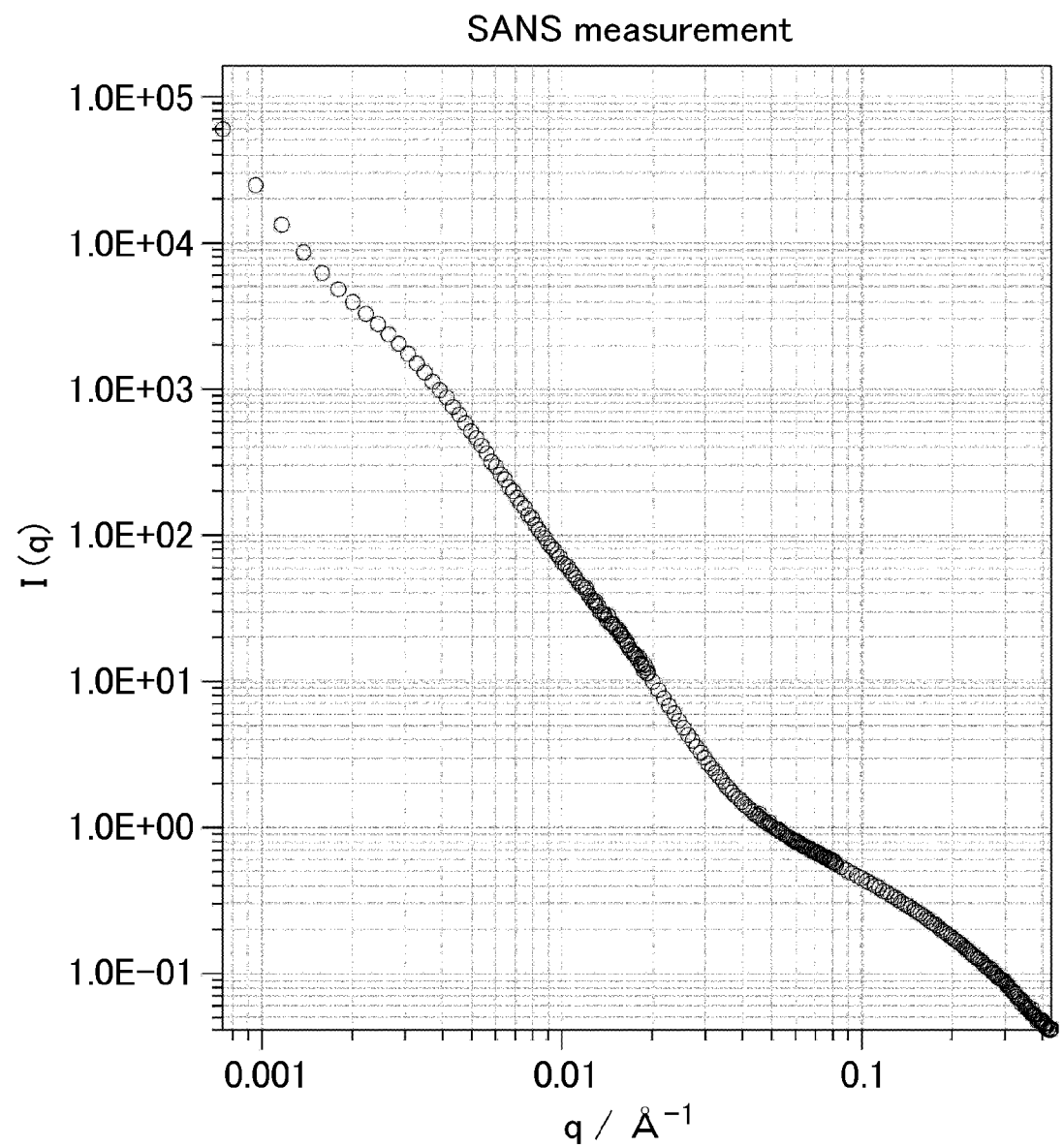

METHOD FOR EVALUATING ENERGY LOSS, CHIPPING RESISTANCE AND ABRASION RESISTANCE OF POLYMERIC MATERIAL

TECHNICAL FIELD

The present invention relates to methods for evaluating energy loss, chipping resistance, and abrasion resistance of a polymeric material.

BACKGROUND ART

Energy loss, chipping resistance, and abrasion resistance of polymeric materials such as rubber materials are important physical quantities that can affect various properties of products formed from these materials. For example, in the case of tires as rubber products, the energy loss is closely related to fuel economy and grip performance, while the chipping resistance and abrasion resistance are closely related to the life of the tires.

As a method for evaluating energy loss in a polymeric material, a technique of measuring the loss tangent (tan δ) by dynamic viscoelasticity measurement is widely used (see Patent Literature 1). However, this technique causes great errors, and its measurement accuracy is insufficient. Another problem is that in the case where differences between samples are small, such differences cannot be evaluated with good reproducibility.

As a method for evaluating chipping resistance or abrasion resistance of a tire, for example, a road test is commonly performed in which the incidence of chipping of a tire tread portion or the groove depth is measured after driving a predetermined distance. However, since such a method requires building of a tire and long-distance driving, there is a demand for an efficient evaluation method that provides measurement in a short period of time and at low cost. Yet, such an efficient method for evaluating chipping resistance is generally unknown.

Further, a Lambourn abrasion test and DIN abrasion test are known as the method for evaluating abrasion resistance in a short period of time and at low cost. However, these methods cause great errors, and their measurement accuracy is insufficient although some degree of correlation is found between results of these tests and road test results. Another problem is that in the case where differences between samples are small, such differences cannot be evaluated with good reproducibility (see Non patent Literature 1).

CITATION LIST

Patent Literature

Patent Literature 1: JP-A 2009-46088

Non Patent Literature

Non patent Literature 1: Nippon Gomu Kyokaishi (the Journal of SRIJ) (vol. 69, No. 11, p. 739, 1996)

SUMMARY OF INVENTION

Technical Problem

The present invention aims to solve the above problems and provide a method for evaluating energy loss in a polymeric material, wherein the method provides sufficient evaluation of the difference in performance between samples with excellent measurement accuracy. The present invention also aims to solve the above problems and provide a method for evaluating chipping resistance of a polymeric material, wherein the method provides evaluation in a short period of time and at low cost with excellent measurement accuracy. Further, the present invention aims to solve the above problems and provide a method for evaluating abrasion resistance of a polymeric material, wherein the method provides sufficient evaluation of the difference in performance between samples with excellent measurement accuracy.

Solution to Problem

A first aspect of the present invention relates to a method for evaluating energy loss in a polymeric material, the method including irradiating the polymeric material with X-rays or neutrons to perform X-ray scattering measurement or neutron scattering measurement.

In the first aspect of the present invention, preferably, the X-ray scattering measurement is small-angle X-ray scattering measurement, and the neutron scattering measurement is small-angle neutron scattering measurement.

In the first aspect of the present invention, the polymeric material is preferably a rubber material formed from at least one conjugated diene compound. Here, the rubber material is preferably a rubber material for tires.

In the method for evaluating energy loss in a polymeric material according to the first aspect of the present invention, measurement is preferably performed using the X-rays or neutrons under a condition where q defined by equation 1-1 is in a range of not more than 10 nm$^{-1}$:

$$q = \frac{4\pi \sin(\theta/2)}{\lambda} \qquad \text{Equation 1-1}$$

(θ: scattering angle; λ: wavelength of X-rays or neutrons).

The method for evaluating energy loss in a polymeric material according to the first aspect of the present invention is preferably a method wherein the energy loss is evaluated based on a correlation length ξ in a range of 1 nm to 100 μm determined by curve fitting equations 1-2 and 1-3 to a scattering intensity curve $I_{(q)}$ obtained by the X-ray scattering measurement or neutron scattering measurement:

$$I_{(q)} = \frac{A}{1+q^2\xi^2} + \frac{B}{(1+q^2\Xi_b^2)^2} + \frac{C}{(1+q^2\Xi_c^2)^2}, \qquad \text{Equation 1-2}$$

$$\xi < \Xi_b < \Xi_c \qquad \text{Equation 1-3}$$

($A$, $B$, $C$, $\xi$, $\Xi_b$, $\Xi_c$: fitting parameters)

($q$: as defined above).

A second aspect of the present invention relates to a method for evaluating chipping resistance of a polymeric material, the method including irradiating the polymeric material with X-rays or neutrons to perform X-ray scattering measurement or neutron scattering measurement.

In the second aspect of the present invention, preferably, the X-ray scattering measurement is small-angle X-ray scattering measurement, and the neutron scattering measurement is small-angle neutron scattering measurement.

In the second aspect of the present invention, the polymeric material is preferably a rubber material formed from at least one conjugated diene compound. Here, the rubber material is preferably a rubber material for tires.

In the method for evaluating chipping resistance of a polymeric material according to the second aspect of the present invention, measurement is preferably performed using the X-rays or neutrons under a condition where q defined by equation 2-1 is in a range of not more than 10 nm$^{-1}$:

$$q = \frac{4\pi \sin(\theta/2)}{\lambda} \qquad \text{Equation 2-1}$$

($\theta$: scattering angle; $\lambda$: wavelength of X-rays or neutrons).

The method for evaluating chipping resistance of a polymeric material according to the second aspect of the present invention is preferably a method wherein the chipping resistance is evaluated based on a correlation length $\Xi_c$ in a range of 1 nm to 100 µm determined by curve fitting equations 2-2 and 2-3 to a scattering intensity curve $I_{(q)}$ obtained by the X-ray scattering measurement or neutron scattering measurement:

$$I_{(q)} = \frac{A}{1+q^2\xi^2} + \frac{B}{(1+q^2\Xi_b^2)^2} + \frac{C}{(1+q^2\Xi_c^2)^2}, \qquad \text{Equation 2-2}$$

$$\xi < \Xi_b < \Xi_c \qquad \text{Equation 2-3}$$

(A, B, C, $\xi$, $\Xi_b$, $\Xi_c$: fitting parameters)
(q: as defined above).

A third aspect of the present invention relates to a method for evaluating abrasion resistance of a polymeric material, the method including irradiating the polymeric material with X-rays or neutrons to perform X-ray scattering measurement or neutron scattering measurement.

In the third aspect of the present invention, preferably, the X-ray scattering measurement is small-angle X-ray scattering measurement, and the neutron scattering measurement is small-angle neutron scattering measurement.

In the third aspect of the present invention, the polymeric material is preferably a rubber material formed from at least one conjugated diene compound. Here, the rubber material is preferably a rubber material for tires.

In the method for evaluating abrasion resistance of a polymeric material according to the third aspect of the present invention, measurement is preferably performed using the X-rays or neutrons under a condition where q defined by equation 3-1 is in a range of not more than 10 nm$^{-1}$:

$$q = \frac{4\pi \sin(\theta/2)}{\lambda} \qquad \text{Equation 3-1}$$

($\theta$: scattering angle; $\lambda$: wavelength of X-rays or neutrons).

The method for evaluating abrasion resistance of a polymeric material according to the third aspect of the present invention is preferably a method wherein the abrasion resistance is evaluated based on a number $N_c$ per unit volume of scatterers having a correlation length $\Xi_c$ in a range of 1 nm to 100 µm determined by curve fitting equations 3-2 to 3-6 to a scattering intensity curve $I_{(q)}$ obtained by the X-ray scattering measurement or neutron scattering measurement:

$$I_{(q)} = \frac{A}{1+q^2\xi^2} + \frac{B}{(1+q^2\Xi_b^2)^2} + \frac{C}{(1+q^2\Xi_c^2)^2}, \qquad \text{Equation 3-2}$$

$$\xi < \Xi_b < \Xi_c, \qquad \text{Equation 3-3:}$$

$$A = 8\pi N_a \sigma^2 \xi^3, \qquad \text{Equation 3-4:}$$

$$B = 4\pi N_b \sigma^2 \Xi_b^2, \qquad \text{Equation 3-5:}$$

$$C = 4\pi N_c \sigma^2 \Xi_c^2 \qquad \text{Equation 3-6:}$$

(A, B, C, $\xi$, $\Xi_b$, $\Xi_c$: fitting parameters)
(q: as defined above)
($N_a$: number of scatterers having correlation length $\xi$ per unit volume (N/cm$^3$))
($N_b$: number of scatterers having correlation length $\xi_b$ per unit volume (N/cm$^3$))
($N_c$: number of scatterers having correlation length $\xi_c$ per unit volume (N/cm$^3$))
($\sigma$: electron density difference (electron·cm$^{-3}$) between scatterer and surrounding matrix material, or scattering length density difference (mm$^{-2}$) between scatterer and surrounding deuterated solvent).

Advantageous Effects of Invention

The first aspect of the present invention provides a method for evaluating energy loss in a polymeric material, the method including irradiating the polymeric material with X-rays or neutrons to perform X-ray scattering measurement or neutron scattering measurement. Accordingly, measurement errors can be reduced and thus the energy loss can be evaluated with high measurement accuracy. Additionally, the method of the first aspect enables highly accurate evaluation of the difference in energy loss between samples whose difference in performance cannot be evaluated with good reproducibility by dynamic viscoelasticity measurement or the like.

The second aspect of the present invention provides a method for evaluating chipping resistance of a polymeric material, the method including irradiating the polymeric material with X-rays or neutrons to perform X-ray scattering measurement or neutron scattering measurement. Accordingly, measurement errors can be reduced and thus the chipping resistance can be evaluated with high measurement accuracy. Additionally, the method of the second aspect enables the chipping resistance to be evaluated easily in a short period of time and at low cost.

The third aspect of the present invention provides a method for evaluating abrasion resistance of a polymeric material, the method including irradiating the polymeric material with X-rays or neutrons to perform X-ray scattering measurement or neutron scattering measurement. Accordingly, measurement errors can be reduced and thus the abrasion resistance can be evaluated with high measurement accuracy. Additionally, the method of the third aspect enables highly accurate evaluation of the difference in abrasion resistance between samples whose difference in performance cannot be evaluated with good reproducibility by a Lambourn abrasion test, DIN abrasion test or the like.

BRIEF DESCRIPTION OF DRAWINGS

FIG. 1 shows an example of scattering intensity curves of samples of Examples 1-4, 2-4, and 3-4 obtained by SAXS measurement.

DESCRIPTION OF EMBODIMENTS

The first aspect of the present invention provides a method for evaluating energy loss in a polymeric material, the method including irradiating the polymeric material with X-rays or neutrons to perform X-ray scattering measurement or neutron scattering measurement.

A polymeric material such as a rubber material containing a filler such as carbon black or silica can be subjected to small-angle X-ray scattering measurement or small-angle neutron scattering measurement to determine the radius of gyration ($R_g$) of a cluster of 1 nm to 100 μm formed by aggregation of the filler in the material. Since the $R_g$ is highly correlated with the energy loss (i.e., the smaller the $R_g$, the less the energy loss), and the number N of scatterers having the $R_g$ is also highly correlated with the energy loss (i.e., the lower the N, the less the energy loss), the energy loss in the polymeric material can be evaluated by the measurement.

In this regard, the energy loss in a rubber material containing a filler is generally considered to be highly affected by dispersibility of the filler in the material as well as by the polymer component; however, the evaluation methods that use $R_g$ or N are to measure dispersibility of filler to evaluate the energy loss, and thus the energy loss in a polymer is not directly evaluated. Hence, the energy loss in a filler-free rubber material may be unable to be evaluated with high accuracy. For example, in the case of evaluation of rubber materials containing fillers of similar dispersibility, the respective energy losses may not be evaluated with high accuracy.

In this context, the method of the first aspect of the present invention has been completed based on the finding that when small-angle X-ray scattering measurement or small-angle neutron scattering measurement is performed to calculate a correlation length ξ in the range of 0.1 nm to 100 μm, which is presumed to correspond to the distance between crosslinking points in a polymer, and correlation lengths $Ξ_b$ and $Ξ_c$ in the range of 0.1 nm to 100 μm, which are presumed to correspond to the size of a heterogeneous network structure in a polymer, the correlation length ξ is highly correlated with the energy loss, i.e., the smaller the ξ, the less the energy loss, even in the case of filler-free polymeric materials. Accordingly, the energy loss in any polymeric material can be evaluated with high accuracy through X-ray or neutron scattering measurement, regardless of the presence or absence of filler.

Here, although the reason for the correlation between the correlation length ξ and the energy loss is not entirely clear, it is presumed that the energy loss decreases with a decrease in the distance between crosslinking points in a polymer in which the distance between crosslinking points is 0.1 nm to 100 μm, because the shorter the distance between crosslinking points, the better the distribution of the crosslinking points, which means that a force is then uniformly applied to the entire rubber material without causing stress concentration.

In the first aspect of the present invention, small-angle X-ray scattering (SAXS (scattering angle: typically, not more than 10 degrees)) measurement in which a polymeric material is irradiated with X-rays to measure the scattering intensity can be suitably employed as the X-ray scattering measurement for evaluating energy loss in a polymeric material. In the small-angle X-ray scattering, structural information of a substance can be obtained by measuring X-rays scattered at small scattering angles among the scattered X-rays resulting from the irradiation of the substance with X-rays. In this way, ordered structures of few nanometers, such as microphase-separated structures, of polymeric materials can be analyzed.

In order to obtain detailed molecular structural information from the SAXS measurement, it is preferred that an X-ray scattering profile with a high S/N ratio be measurable. For this reason, the X-rays emitted from a synchrotron preferably have a brilliance of at least $10^{10}$ (photons/s/mrad$^2$/mm$^2$/0.1% bw). The "bw" refers to the band width of X-rays emitted from a synchrotron. Examples of such synchrotrons include BL03XU and BL20XU, which are beamlines at the large-scale synchrotron radiation facility SPring-8 of the Japan Synchrotron Radiation Research Institute.

The brilliance (photons/s/mrad$^2$/mm$^2$/0.1% bw) of the X-rays is preferably $10^{10}$ or more, and more preferably $10^{12}$ or more. Although the upper limit is not particularly limited, the intensity of the X-rays is preferably within a range that does not cause radiation damage.

Also, the number of photons (photons/s) in the X-rays is preferably $10^7$ or more, and more preferably $10^9$ or more. Although the upper limit is not particularly limited, the intensity of the X-rays is preferably within a range that does not cause radiation damage.

Additionally, in the first aspect of the present invention, small-angle neutron scattering (SANS (scattering angle: typically, not more than 10 degrees)) measurement in which a polymeric material is irradiated with neutrons to measure the scattering intensity can be suitably employed as the neutron scattering measurement for evaluating energy loss in a polymeric material. In the small-angle neutron scattering, structural information of a substance can be obtained by measuring neutrons scattered at small scattering angles among the scattered neutrons resulting from the irradiation of the substance with neutrons. In this way, ordered structures of few nanometers, such as microphase-separated structures, of polymeric materials can be analyzed.

For the SANS measurement, known methods that use magnetic structures or deuteration techniques can be used. In the case where a deuteration technique is used, for example, a polymeric material is swollen in a deuterated solvent, and the polymeric material in equilibrium in the deuterated solvent is then irradiated with neutrons to measure the scattering intensity. Here, examples of deuterated solvents used to swell the polymeric material include heavy water, deuterated hexane, deuterated toluene, deuterated chloroform, deuterated methanol, deuterated DMSO (($D_3C$)$_2$S=O), deuterated tetrahydrofuran, deuterated acetonitrile, deuterated dichloromethane, deuterated benzene, and deuterated N,N-dimethylformamide.

The neutron beam used for neutron scattering measurement such as SANS may be obtained from, for example, SANS-J, which is a beamline at JRR-3 of the Japan Atomic Energy Agency, an independent administrative agency.

The flux density of the neutrons (neutrons/cm$^2$/s) is preferably $10^3$ or more, and more preferably $10^4$ or more, for obtaining a neutron scattering profile with a high S/N ratio as is the case of the SAXS measurement. Although the upper limit is not particularly limited, the neutron flux density is preferably within a range that does not cause radiation damage.

The X-ray or neutron scattering measurement is preferably performed using the X-rays or neutrons under a condition where q defined by equation 1-1 is in the range of not more than 10 nm$^{-1}$, for the need to measure finer molecular structures of the polymeric material. This q range (nm$^{-1}$) is preferred because a greater numerical value provides finer pieces of information. Thus, q is more preferably in the range of not more than 20 nm$^{-1}$.

$$q = \frac{4\pi\sin(\theta/2)}{\lambda} \qquad \text{Equation 1-1}$$

($\theta$: scattering angle; $\lambda$: wavelength of X-rays or neutrons)

The X-rays scattered in the SAXS measurement are detected by an X-ray detector, and an image is then generated by an image processor or the like using X-ray detection data from the X-ray detector.

Examples of X-ray detectors include two-dimensional detectors (e.g., X-ray film, nuclear emulsion plate, X-ray pickup tube, X-ray fluorescent amplifier tube, X-ray image intensifier, X-ray imaging plate, CCD X-ray detector, amorphous X-ray detectors, etc.) and line sensors (one-dimensional detectors). The X-ray detector may be appropriately selected according to the type and conditions of a polymeric material to be analyzed.

Any ordinary image processor that can generate X-ray scattering images based on X-ray detection data from the X-ray detector can be appropriately used.

The SANS measurement can also be performed based on the same principle as in the SAXS measurement. The scattered neutrons are detected by a neutron detector, and an image is then generated by an image processor or the like using neutron detection data from the neutron detector. Here, as is the case described above, any known two-dimensional detector or one-dimensional detector can be used as the neutron detector, and any known image processor that can generate neutron scattering images can be used. These devices may be appropriately selected.

The polymeric material in the first aspect of the present invention is not particularly limited and may be any conventionally known polymeric material. Examples include rubber materials formed from at least one conjugated diene compound, and composite materials in which the rubber materials are combined with at least one resin. The conjugated diene compound is not particularly limited. Examples thereof include known compounds such as isoprene and butadiene.

Examples of such rubber materials include polymers containing double bonds, such as natural rubber (NR), isoprene rubber (IR), butadiene rubber (BR), styrene butadiene rubber (SBR), acrylonitrile butadiene rubber (NBR), chloroprene rubber (CR), butyl rubber (IIR), halogenated butyl rubber (X-IIR), and styrene isoprene butadiene rubber (SIBR). The polymeric materials such as rubber materials and composite materials mentioned above may contain at least one modifying group such as a hydroxyl or amino group.

The resin is not particularly limited. Examples thereof include resins widely used in the rubber industry, such as C5 aliphatic petroleum resins, cyclopentadiene petroleum resins, and other petroleum resins.

Suitable examples of polymeric materials include rubber materials and composite materials, which contain at least one metal-coordinating functional group in their molecular structure. Here, any metal-coordinating functional group can be used and examples thereof include functional groups containing a metal-coordinating atom such as oxygen, nitrogen, or sulfur. Specific examples include a dithiocarbamic acid group, phosphoric acid group, carboxylic acid group, carbamic acid group, dithioic acid group, aminophosphoric acid group, and thiol group. The polymeric material may contain only one or two or more types of functional groups mentioned above.

Examples of metals that coordinate to the functional group(s) include Fe, Cu, Ag, Co, Mn, Ni, Ti, V, Zn, Mo, W, Os, Mg, Ca, Sr, Ba, Al, and Si. For example, in the case of a polymeric material that includes a compound containing such a metal atom ($M_1$) and also contains a metal-coordinating functional group (such as —COO), each —COOM$_1$ binds to each other by coordinate bonds, resulting in overlapping of many —COOM$_1$ groups and thereby forming clusters of aggregated metal atoms. The amount of the metal atom ($M_1$) is preferably 0.01 to 200 parts by mass per 100 parts by mass of the polymer component of the polymeric material.

Suitable examples of polymeric materials also include rubber materials and composite materials, which contain fillers. Here, examples of fillers include carbon black and silica; and fillers represented by $mM_2 \cdot xSiO_y \cdot zH_2O$ (wherein $M_2$ represents at least one metal selected from the group consisting of aluminum, calcium, magnesium, titanium, and zirconium; or an oxide, hydroxide, hydrate, or carbonate of the metal; m represents a number of 1 to 5; x represents a number of 0 to 10; y represents a number of 2 to 5; and z represents a number of 0 to 10).

Specific examples of fillers represented by $mM_2 \cdot xSiO_y \cdot zH_2O$ include aluminum hydroxide ($Al(OH)_3$), alumina ($Al_2O_3$, $Al_2O_3 \cdot 3H_2O$ (hydrate)), clay ($Al_2O_3 \cdot 2SiO_2$), kaolin ($Al_2O_3 \cdot 2SiO_2 \cdot 2H_2O$) pyrophyllite ($Al_2O_3 \cdot 4SiO_2 \cdot H_2O$), bentonite ($Al_2O_3 \cdot 4SiO_2 \cdot 2H_2O$), aluminium silicate ($Al_2SiO_5$, $Al_4(SiO_2)_3 \cdot 5H_2O$, and the like), calcium aluminium silicate ($Al_2O_3 \cdot CaO \cdot 2SiO_2$), calcium hydroxide ($Ca(OH)_2$), calcium oxide ($CaO$), calcium silicate ($Ca_2SiO_4$), magnesium calcium silicate ($CaMgSiO_4$), magnesium hydroxide ($Mg(OH)_2$), magnesium oxide ($MgO$), talc ($MgO \cdot 4SiO_2 H_2O$), attapulgite ($5MgO \cdot 8SiO_2 \cdot 9H_2O$), aluminum magnesium oxide ($MgO \cdot Al_2O_3$), titanium while ($TiO_2$), and titanium black ($Ti_nO_{2n-1}$). Aggregated filler clusters can be formed in polymeric materials containing such fillers. The amount of the filler is preferably 10 to 200 parts by mass per 100 parts by mass of the polymer component of the polymeric material.

The rubber materials and composite materials may contain other additives generally used in the field of rubber industry (e.g. silane coupling agents, zinc oxides, stearic acid, various antioxidants, oils, waxes, vulcanizing agents, vulcanization accelerators, and crosslinking agents). These rubber materials and composite materials can be prepared by a known kneading method and the like. Examples of these rubber materials and composite materials include those used as rubber materials for tires.

Next is a specific explanation of a method for analyzing a scattering intensity curve obtained by the X-ray scattering measurement or neutron scattering measurement of a polymeric material.

A scattering intensity curve of a polymeric material obtained by SAXS measurement or SANS measurement can be analyzed, for example, by the following method to thereby determine the correlation length $\xi$ in the range of 1 nm to 100 μm (the distance between crosslinking points in the polymer).

A scattering intensity curve $I_{(q)}$ obtained by SAXS measurement or SANS measurement as shown in FIG. 1 is curve fitted with equations 1-2 and 1-3, and fitting parameters are then determined by least squares.

$$I_{(q)} = \frac{A}{1+q^2\xi^2} + \frac{B}{(1+q^2\Xi_b^2)^2} + \frac{C}{(1+q^2\Xi_c^2)^2} \qquad \text{Equation 1-2}$$

$$\xi < \Xi_b < \Xi_c \qquad \text{Equation 1-3}$$

($A$, $B$, $C$, $\xi$, $\Xi_b$, $\Xi_c$: fitting parameters)

($q$: as defined above)

Among the obtained fitting parameters, the correlation length ξ in the range of 1 nm to 100 μm is presumed to correspond to the distance between crosslinking points in a polymer, and the correlation lengths $\Xi_b$ and $\Xi_c$ are presumed to correspond to the size of a heterogeneous network structure in a polymer. As described above, the correlation length ξ is highly correlated with the energy loss, i.e., the smaller the ξ, the less the energy loss. Thus, the is considered to have a great influence on the energy loss. Accordingly, the energy loss in any polymeric material can be evaluated, regardless of the presence or absence of filler, by performing X-ray scattering measurement such as SAXS or neutron scattering measurement such as SANS and then determining ξ by curve fitting with equations 1-2 and 1-3.

The energy loss in the polymer itself can be taken into consideration by the first aspect of the present invention, particularly, the evaluation method that uses the correlation length ξ. Accordingly, the energy loss not only in rubber materials containing filler but also in filler-free rubber materials and the like can be evaluated with high accuracy. Additionally, the first aspect enables highly accurate evaluation of the difference in energy loss between samples whose difference in performance cannot be evaluated with good reproducibility by dynamic viscoelasticity measurement or the like.

Next, the second aspect of the present invention provides a method for evaluating chipping resistance of a polymeric material, the method including irradiating the polymeric material with X-rays or neutrons to perform X-ray scattering measurement or neutron scattering measurement.

The method of the second aspect of the present invention has been completed based on the finding that when small-angle X-ray scattering measurement or small-angle neutron scattering measurement is performed on a polymeric material such as a rubber material to calculate a correlation length ξ in the range of 0.1 nm to 100 μm, which is presumed to correspond to the distance between crosslinking points in a polymer, and correlation lengths $\Xi_b$ and $\Xi_c$ in the range of 0.1 nm to 100 μm, which are presumed to correspond to the size of a heterogeneous network structure in a polymer, the correlation length $\Xi_c$ is highly correlated with the chipping resistance, i.e., the smaller the $\Xi_c$, the better the chipping resistance. Accordingly, the chipping resistance of a polymeric material can be easily evaluated with high accuracy through X-ray or neutron scattering measurement.

Here, although the reason for the correlation between the correlation length $\Xi_c$ and the chipping resistance is not entirely clear, it is presumed that the chipping resistance improves with a decrease in the size of a heterogeneous network structure in a polymer because chipping starts from a heterogeneous network structure of 0.1 nm to 100 μm in a polymer, which means that the smaller the heterogeneous structure in the polymer, the less likely chipping starts therefrom.

In the second aspect of the present invention, small-angle X-ray scattering (SAXS (scattering angle: typically, not more than 10 degrees)) measurement in which a polymeric material is irradiated with X-rays to measure the scattering intensity can be suitably employed as the X-ray scattering measurement for evaluating chipping resistance of a polymeric material. In the small-angle X-ray scattering, structural information of a substance can be obtained by measuring X-rays scattered at small scattering angles among the scattered X-rays resulting from the irradiation of the substance with X-rays. In this way, ordered structures of few nanometers, such as microphase-separated structures, of polymeric materials can be analyzed.

In order to obtain detailed molecular structural information from the SAXS measurement, it is preferred that an X-ray scattering profile with a high S/N ratio be measurable. For this reason, the X-rays emitted from a synchrotron preferably have a brilliance of at least $10^{10}$ (photons/s/mrad$^2$/mm$^2$/0.1% bw). The "bw" refers to the band width of X-rays emitted from a synchrotron. Examples of such synchrotrons include BL03XU and BL20XU, which are beamlines at the large-scale synchrotron radiation facility SPring-8 of the Japan Synchrotron Radiation Research Institute.

In the second aspect of the present invention, the brilliance of the X-rays and the number of photons in the X-rays are preferably the same as those in the first aspect of the present invention.

Additionally, in the second aspect of the present invention, small-angle neutron scattering (SANS (scattering angle: typically, not more than 10 degrees)) measurement in which a polymeric material is irradiated with neutrons to measure the scattering intensity can be suitably employed as the neutron scattering measurement for evaluating chipping resistance of a polymeric material. In the small-angle neutron scattering, structural information of a substance can be obtained by measuring neutrons scattered at small scattering angles among the scattered neutrons resulting from the irradiation of the substance with neutrons. In this way, ordered structures of few nanometers, such as microphase-separated structures, of polymeric materials can be analyzed.

For the SANS measurement, known methods that use magnetic structures or deuteration techniques can be used, as is the case with the first aspect of the present invention. Also, the flux density of the neutrons may be the same as in the first aspect.

The X-ray or neutron scattering measurement is preferably performed using the X-rays or neutrons under a condition where q defined by equation 2-1 is in the range of not more than 10 nm$^{-1}$, for the need to measure finer molecular structures of the polymeric material. This q range (nm$^{-1}$) is preferred because a greater numerical value provides finer pieces of information. Thus, q is more preferably in the range of not more than 20 nm$^{-1}$.

$$q = \frac{4\pi \sin(\theta/2)}{\lambda} \quad \text{Equation 2-1}$$

(θ: scattering angle; λ: wavelength of X-rays or neutrons)

The X-rays scattered in the SAXS measurement and the neutrons scattered in the SANS measurement can be measured by the same principle as in the first aspect of the present invention.

In the second aspect of the present invention, the polymeric material is not particularly limited. Examples thereof include those mentioned in the first aspect of the present invention. The amount of the metal atom ($M_1$) and the amount of the filler are also preferably in the same ranges as described above.

The polymeric material may also contain other additives as described in the first aspect of the present invention. Moreover, the polymeric material can be prepared by the same method, and it may be a rubber material for tires or the like.

Next is a specific explanation of a method for analyzing a scattering intensity curve obtained by the X-ray scattering measurement or neutron scattering measurement of a polymeric material.

A scattering intensity curve of a polymeric material obtained by SAXS measurement or SANS measurement can be analyzed, for example, by the following method to thereby determine the correlation length $\Xi_c$ in the range of 1 nm to 100 μm (the size of a heterogeneous network structure in the polymer).

A scattering intensity curve $I_{(q)}$ obtained by SAXS measurement or SANS measurement as shown in FIG. 1 is curve fitted with equations 2-2 and 2-3, and fitting parameters are then determined by least squares.

$$I_{(q)} = \frac{A}{1+q^2\xi^2} + \frac{B}{(1+q^2\Xi_b^2)^2} + \frac{C}{(1+q^2\Xi_c^2)^2} \qquad \text{Equation 2-2}$$

$$\xi < \Xi_b < \Xi_c \qquad \text{Equation 2-3}$$

($A$, $B$, $C$, $\xi$, $\Xi_b$, $\Xi_c$: fitting parameters)
($q$: as defined above)

Among the obtained fitting parameters, the correlation length $\xi$ in the range of 1 nm to 100 μm is presumed to correspond to the distance between crosslinking points in a polymer, and the correlation lengths $\Xi_b$ and $\Xi_c$ are presumed to correspond to the size of a heterogeneous network structure in a polymer. As described above, the correlation length $\Xi_c$ is highly correlated with the chipping resistance, i.e., the smaller the $\Xi_c$, the better the chipping resistance. Thus, the $\Xi_c$ is considered to have a great influence on the chipping resistance. Accordingly, the chipping resistance of a polymeric material can be evaluated by performing X-ray scattering measurement such as SAXS or neutron scattering measurement such as SANS and then determining $\Xi_c$ by curve fitting with equations 2-2 and 2-3.

The heterogeneity of the crosslinked structure of the polymer can be taken into consideration by the second aspect of the present invention, particularly, the evaluation method that uses the correlation length $\Xi_c$. Accordingly, the chipping resistance of rubber materials and the like can be evaluated with high accuracy. Additionally, the second aspect enables the chipping resistance to be easily evaluated without building a tire and carrying out a road test. Thus, efficient development is enabled.

Next, the third aspect of the present invention provides a method for evaluating abrasion resistance of a polymeric material, the method including irradiating the polymeric material with X-rays or neutrons to perform X-ray scattering measurement or neutron scattering measurement.

The method of the third aspect of the present invention has been completed based on the finding that when small-angle X-ray scattering measurement or small-angle neutron scattering measurement is performed on a polymeric material such as a rubber material to calculate a correlation length $\xi$ in the range of 0.1 nm to 100 μm, which is presumed to correspond to the distance between crosslinking points in a polymer, and correlation lengths $\Xi_b$ and $\Xi_c$ in the range of 0.1 nm to 100 μm, which are presumed to correspond to the size of a heterogeneous network structure in a polymer, the abrasion resistance is highly correlated with a number $N_c$, of scatterers (heterogeneous network structures) having the correlation length $\Xi_c$ per unit volume, i.e., the higher the $N_c$, the better the abrasion resistance. Accordingly, the abrasion resistance of a polymeric material can be evaluated with high accuracy through X-ray or neutron scattering measurement.

Here, although the reason for the correlation between the number $N_c$ and the abrasion resistance is not entirely clear, it is presumed that the abrasion resistance improves with an increase in the number of heterogeneous network structures having the correlation length $\Xi_c$ in the range of 0.1 nm to 100 μm because the heterogeneous network structures play a role of suppressing crack growth, which means that the greater the number of heterogeneous network structures, the more suppressed the crack growth.

In the third aspect of the present invention, small-angle X-ray scattering (SAXS (scattering angle: typically, not more than 10 degrees)) measurement in which a polymeric material is irradiated with X-rays to measure the scattering intensity can be suitably employed as the X-ray scattering measurement for evaluating abrasion resistance of a polymeric material. In the small-angle X-ray scattering, structural information of a substance can be obtained by measuring X-rays scattered at small scattering angles among the scattered X-rays resulting from the irradiation of the substance with X-rays. In this way, ordered structures of few nanometers, such as microphase-separated structures, of polymeric materials can be analyzed.

In order to obtain detailed molecular structural information from the SAXS measurement, it is preferred that an X-ray scattering profile with a high S/N ratio be measurable. For this reason, the X-rays emitted from a synchrotron preferably have a brilliance of at least $10^{10}$ (photons/s/mrad$^2$/mm$^2$/0.1% bw). The "bw" refers to the band width of X-rays emitted from a synchrotron. Examples of such synchrotrons include BL03XU and BL20XU, which are beamlines at the large-scale synchrotron radiation facility SPring-8 of the Japan Synchrotron Radiation Research Institute.

In the third aspect of the present invention, the brilliance of the X-rays and the number of photons in the X-rays are preferably the same as those in the first aspect of the present invention.

Also in the third aspect of the present invention, small-angle neutron scattering (SANS (scattering angle: typically, not more than 10 degrees)) measurement in which a polymeric material is irradiated with neutrons to measure the scattering intensity can be suitably employed as the neutron scattering measurement for evaluating abrasion resistance of a polymeric material. In the small-angle neutron scattering, structural information of a substance can be obtained by measuring neutrons scattered at small scattering angles among the scattered neutrons resulting from the irradiation of the substance with neutrons. In this way, ordered structures of few nanometers, such as microphase-separated structures, of polymeric materials can be analyzed.

For the SANS measurement, known methods that use magnetic structures or deuteration techniques can be used, as in the case with the first aspect of the present invention. Also, the flux density of the neutrons may be the same as in the first aspect.

The X-ray or neutron scattering measurement is preferably performed using the X-rays or neutrons under a condition where q defined by equation 3-1 is in the range of not more than 10 nm$^{-1}$, for the need to measure finer molecular structures of the polymeric material. This q range (nm$^{-1}$) is preferred because a greater numerical value provides finer pieces of information. Thus, q is more preferably in the range of not more than 20 nm$^{-1}$.

$$q = \frac{4\pi\sin(\theta/2)}{\lambda} \qquad \text{Equation 3-1}$$

($\theta$: scattering angle; $\lambda$: wavelength of X-rays or neutrons)

The X-rays scattered in the SAXS measurement and the neutrons scattered in the SANS measurement can be measured by the same principle as in the first aspect of the present invention.

In the third aspect of the present invention, the polymeric material is not particularly limited. Examples thereof include those mentioned in the first aspect of the present invention. The amount of the metal atom ($M_1$) and the amount of the filler are also preferably in the same ranges as described above.

The polymeric material may also contain other additives as described in the first aspect of the present invention. Moreover, the polymeric material can be prepared by the same method as in the first aspect, and it may be a rubber material for tires or the like.

Next is a specific explanation of a method for analyzing a scattering intensity curve obtained by the X-ray scattering measurement or neutron scattering measurement of a polymeric material.

A scattering intensity curve of a polymeric material obtained by SAXS measurement or SANS measurement is analyzed, for example, by the following method to thereby determine the number $N_c$ of scatterers (heterogeneous network structures) having the correlation length $\Xi_c$ in the range of 1 nm to 100 μm per unit volume.

A scattering intensity curve $I_{(q)}$ obtained by SAXS measurement or SANS measurement as shown in FIG. 1 is curve fitted with equations 3-2 to 3-6, and fitting parameters are then determined by least squares.

$$I_{(q)} = \frac{A}{1+q^2\xi^2} + \frac{B}{(1+q^2\Xi_b^2)^2} + \frac{C}{(1+q^2\Xi_c^2)^2} \quad \text{Equation 3-2}$$

$$\xi < \Xi_b < \Xi_c \quad \text{Equation 3-3:}$$

$$A = 8\pi N_a \sigma^2 \xi^3 \quad \text{Equation 3-4:}$$

$$B = 4\pi N_b \sigma^2 \Xi_b^2 \quad \text{Equation 3-5:}$$

$$C = 4\pi N_c \sigma^2 \Xi_c^2 \quad \text{Equation 3-6:}$$

(A, B, C, $\xi$, $\Xi_b$, $\Xi_c$: fitting parameters)
(q: as defined above)
($N_a$: number of scatterers having correlation length $\xi$ per unit volume (N/cm$^3$))
($N_b$: number of scatterers having correlation length $\Xi_b$ per unit volume (N/cm$^3$))
($N_c$: number of scatterers having correlation length $\Xi_c$ per unit volume (N/cm$^3$))
($\sigma$: electron density difference (electron·cm$^{-3}$) between scatterer and surrounding matrix material, or scattering length density difference (cm$^{-2}$) between scatterer and surrounding deuterated solvent)

Among the obtained fitting parameters, the correlation length $\xi$ in the range of 1 nm to 100 μm is presumed to correspond to the distance between crosslinking points in a polymer, and the correlation lengths $\Xi_b$ and $\Xi_c$ are presumed to correspond to the size of a heterogeneous network structure in a polymer. As described above, the number $N_c$ of scatterers (heterogeneous network structures) having the correlation length $\Xi_c$ per unit volume is highly correlated with the abrasion resistance, i.e., the higher the $N_c$, the better the abrasion resistance. Thus, $N_c$ is considered to have a great influence on the abrasion resistance. Accordingly, the abrasion resistance of a polymeric material can be evaluated by performing X-ray scattering measurement such as SAXS or neutron scattering measurement such as SANS and then determining $N_c$ by curve fitting with equations 3-2 to 3-6.

The heterogeneity of the crosslinked structure of the polymer can be taken into consideration by the third aspect of the present invention, particularly, the evaluation method that uses the number $N_c$ of scatterers (heterogeneous network structures) having the correlation length $\Xi_c$ in the range of 1 nm to 100 μm per unit volume. Accordingly, the abrasion resistance of rubber materials and the like can be evaluated with high accuracy. Additionally, the third aspect enables highly accurate evaluation of the difference in abrasion resistance between samples whose difference in performance cannot be evaluated with good reproducibility by a Lambourn abrasion test, DIN abrasion test or the like.

EXAMPLES

The present invention is now more specifically described with reference to examples but is not limited thereto.

The chemical agents used in Examples and Comparative Examples are listed below.

(Chemical Agents Used)
Cyclohexane: available from Kanto Chemical Co., Inc.
Pyrrolidine: available from Kanto Chemical Co., Inc.
Divinylbenzene: available from Sigma-Aldrich Japan K.K.
1.6 M n-butyllithium in hexane: available from Kanto Chemical Co., Inc.
Isopropanol: available from Kanto Chemical Co., Inc.
Styrene: available from Kanto Chemical Co., Inc.
Butadiene: available from Takachiho Chemical Industrial Co., Ltd.
Tetramethylethylenediamine: available from Kanto Chemical Co., Inc.
Modifier: 3-(N,N-dimethylaminopropyl)trimethoxysilane available from AZmax. Co.
NR: RSS#3
Carbon black: N220 available from Cabot Corporation
Aromatic oil: Diana Process AH-24 available from Idemitsu Kosan Co., Ltd.
Stearic acid: stearic acid available from NOF Corporation
Zinc oxide: Ginrei R available from Toho Zinc Co., Ltd.
Antioxidant: Nocrac 6C (N-(1,3-dimethylbutyl)-N'-phenyl-p-phenylenediamine) available from Ouchi Shinko Chemical Industrial Co., Ltd.
Wax: Sunnoc Wax available from Ouchi Shinko Chemical Industrial Co., Ltd.
Sulfur: powdered sulfur available from Tsurumi Chemical Industry Co., Ltd.
Vulcanization accelerator (1): Nocceler CZ available from Ouchi Shinko Chemical Industrial Co., Ltd.
Vulcanization accelerator (2): Nocceler D available from Ouchi Shinko Chemical Industrial Co., Ltd.

(Synthesis of Monomer (1))

A sufficiently nitrogen-purged vessel (100-mL) was charged with 50 mL of cyclohexane, 4.1 mL of pyrrolidine, and 8.9 mL of divinylbenzene. Further, 0.7 mL of 1.6 M n-butyllithium in hexane was added to the vessel at 0° C., and the mixture was stirred. After one hour, isopropanol was added thereto to terminate the reaction. The reaction mixture was extracted and purified to thereby obtain monomer (1).

(Synthesis of Polymer (1))

A sufficiently nitrogen-purged, pressure-resistant vessel (1000-mL) was charged with 600 mL of cyclohexane, 12.6 mL of styrene, 71.0 mL of butadiene, 0.06 g of monomer (1), and 0.11 mL of tetramethylethylenediamine. Further, 0.2 mL of 1.6 M n-butyllithium in hexane was added to the vessel at 40° C., and the mixture was stirred. After three hours, 0.5 mL of the modifier was added to the mixture, and the resulting mixture was stirred. After one hour, 3 mL of isopropanol was added thereto to terminate the polymerization. After addition of 1 g of 2,6-di-tert-butyl-p-cresol to the reaction solution, the reaction solution was reprecipitated with methanol and dried with heat to thereby obtain polymer (1).
(Synthesis of Polymer (2))
Polymer (2) was obtained by the same method used to obtain polymer (1), except that the amount of monomer (1) was 0.17 g.
(Synthesis of Polymer (3))
Polymer (3) was obtained by the same method used to obtain polymer (1), except that the amount of monomer (1) was 0.29 g.
(Method for Preparing Molded Product)
According to each composition shown in Tables 1 to 3, ingredients were kneaded in a Banbury mixer and a roll mixer, and the mixture was then press-molded at 170° C. for 20 minutes into a molded product.

The energy loss, chipping resistance, and abrasion resistance of the obtained molded products were evaluated by the following test methods: SAXS measurement method, dynamic viscoelasticity measurement method, Lambourn abrasion test, and road test. The results are given in the tables.

1-1. SANS Measurement Method—Correlation Length $\xi$

Examples 1-1 to 1-6

A plate-like sample (molded product) having a thickness of about 1 mm was swollen to equilibrium in deuterated toluene, and attached to a sample holder. The sample was then irradiated with neutrons at room temperature. Absolute scattering intensity curves obtained by measuring the sample at distances of 2.5 m, 10 m, and 10 m with a focusing lens from the detector were combined by least squares. These three curves were combined in the following manner: the scattering intensity curve obtained by measuring the sample at a distance of 2.5 m from the detector was fixed, and the scattering intensity curves obtained by measuring the sample at a distance of 10 m with and without a focusing lens from the detector were shifted. The thus obtained scattering intensity curve $I_{(q)}$ was curve fitted with equations 1-2 and 1-3, and a fitting parameter (correlation length in the range of 1 nm to 100 μm (distance between crosslinking points in the polymer)) was then determined by least squares. The obtained value of correlation length $\xi$ was expressed as an index, with the value determined in Example 1-1 as 100. A higher index value indicates less energy loss.

(SANS Device)
SANS: SANS device in SANS-J, which is a beamline at JRR-3 of the Japan Atomic Energy Agency, an independent administrative agency.
(Measurement Conditions)
Neutron wavelength: 6.5 Å
Flux density of neutrons: $9.9 \times 10^7$ neutrons/cm$^2$/s
Distance from sample to detector: 2.5 m and 10 m (in order to obtain information at smaller angles, the sample was measured at a distance of 10 m from the detector, using a focusing lens.)
(Detector)
Two-dimensional detector ($^3$He 2d detector and two-dimensional photomultiplier tube+ZnS/$^6$LiF detector)

1-2. Dynamic Viscoelasticity Measurement Method

Comparative Examples 1-1 to 1-6

A spectrometer available from Ueshima Seisakusho Co., Ltd. was used to measure the tan δ at a dynamic strain amplitude of 1%, a frequency of 10 Hz, and a temperature of 60° C. The reciprocal of the determined tan δ was expressed as an index, with the value of Comparative Example 1-1 as 100. A higher index value indicates less energy loss.

1-3. Tire Rolling Performance

Test tires including tire components formed from the compositions of Examples 1-1 to 1-6 and Comparative Examples 1-1 to 1-6 were run with a rim of 15×6JJ at an internal pressure of 230 kPa, a load of 3.43 kN, and a speed of 80 km/h in a rolling resistance tester to measure the rolling resistance. The rolling resistance was expressed as an index, with the value of Comparative Example 1-1 as 100. A higher index value indicates better rolling performance of the tire and less energy loss.

TABLE 1

| | | Examples | | | | | | Comparative Examples | | | | | |
|---|---|---|---|---|---|---|---|---|---|---|---|---|---|
| | | 1-1 | 1-2 | 1-3 | 1-4 | 1-5 | 1-6 | 1-1 | 1-2 | 1-3 | 1-4 | 1-5 | 1-6 |
| Composition (part(s) by mass) | NR | 30 | 30 | 30 | 30 | 30 | 30 | 30 | 30 | 30 | 30 | 30 | 30 |
| | Polymer (1) | 70 | — | — | 70 | — | — | 70 | — | — | 70 | — | — |
| | Polymer (2) | — | 70 | — | — | 70 | — | — | 70 | — | — | 70 | — |
| | Polymer (3) | — | — | 70 | — | — | 70 | — | — | 70 | — | — | 70 |
| | Carbon black | 50 | 50 | 50 | — | — | — | 50 | 50 | 50 | — | — | — |
| | Aromatic oil | 20 | 20 | 20 | 20 | 20 | 20 | 20 | 20 | 20 | 20 | 20 | 20 |
| | Stearic acid | 2 | 2 | 2 | 2 | 2 | 2 | 2 | 2 | 2 | 2 | 2 | 2 |
| | Zinc oxide | 3 | 3 | 3 | 3 | 3 | 3 | 3 | 3 | 3 | 3 | 3 | 3 |
| | Antioxidant | 1 | 1 | 1 | 1 | 1 | 1 | 1 | 1 | 1 | 1 | 1 | 1 |
| | Wax | 1 | 1 | 1 | 1 | 1 | 1 | 1 | 1 | 1 | 1 | 1 | 1 |
| | Sulfur | 1.5 | 1.5 | 1.5 | 1.5 | 1.5 | 1.5 | 1.5 | 1.5 | 1.5 | 1.5 | 1.5 | 1.5 |
| | Vulcanization accelerator (1) | 1 | 1 | 1 | 1 | 1 | 1 | 1 | 1 | 1 | 1 | 1 | 1 |
| | Vulcanization accelerator (2) | 0.5 | 0.5 | 0.5 | 0.5 | 0.5 | 0.5 | 0.5 | 0.5 | 0.5 | 0.5 | 0.5 | 0.5 |
| Energy loss index | Small-angle scattering measurement method ($\xi$) | 100 | 129 | 194 | 81 | 88 | 95 | — | — | — | — | — | — |
| | Dynamic viscoelasticity measurement method | — | — | — | — | — | — | 100 | 100 | 101 | 75 | 75 | 76 |
| | Tire rolling performance | 100 | 108 | 124 | 62 | 66 | 74 | 100 | 108 | 124 | 62 | 66 | 74 |

According to Table 1, the examples in which SANS measurement was used demonstrated that the energy loss can be evaluated by determining the correlation length $\xi$ by curve fitting with equations 1-2 and 1-3. In particular, in comparison with the comparative examples, it is clear that the SANS measurement method provides highly accurate measurement of a small difference in energy loss between samples, which is difficult to evaluate by the dynamic viscoelasticity measurement method. Further, it is clear from the results of the carbon black-free compositions of Examples 1-4 to 1-6 that the energy loss in filler-free compositions can also be successfully evaluated by measuring the correlation length ξ.

2-1. SANS Measurement Method—Correlation Length $\Xi_c$

Examples 2-1 to 2-6

The scattering intensity curve $I_{(q)}$ obtained by the SANS measurement method was curve fitted with equations 2-2 and 2-3, and a fitting parameter $\Xi_c$ (correlation length ξ in the range of 1 nm to 100 μm (size of a heterogeneous network structure in the polymer)) was then determined by least squares. The obtained value of correlation length $\Xi_c$ was expressed as an index, with the value determined in Example 2-1 as 100. A lower index value indicates higher chipping resistance.

2-2. Chipping Test on the Road

Comparative Examples 2-1 to 2-6

Test tires (tire size: 195/65R15) including tire tread portions formed from the compositions of Comparative Examples 2-1 to 2-6 were each mounted on a Japanese FF (front-engine, front-wheel drive) car, and the number of chipped spots in the tire tread portion of each tire after driving 8000 km was counted. The determined number was expressed as an index, with the value of Comparative Example 1-1 as 100. A lower index value indicates higher chipping resistance.

road test results of the comparative examples. This clearly shows that the SANS measurement method provides highly accurate evaluation. It is also clear that the chipping resistance can be successfully evaluated regardless of the presence or absence of carbon black.

3-1. SANS Measurement Method—Number $N_c$

Examples 3-1 to 3-6

The scattering intensity curve $I_{(q)}$ obtained by the SANS measurement method was curve fitted with equations 3-2 to 3-6, and a fitting parameter $\Xi_c$ (correlation length in the range of 1 nm to 100 μm (size of a heterogeneous network structure in the polymer)) was then determined by least squares. Further, the number $N_c$ of scatterers having the correlation length $\Xi_c$ per unit volume was determined based on the obtained value of correlation length $\Xi_c$. The determined value of $N_c$ was expressed as an index, with the value of Example 3-1 as 100. A higher index value indicates higher abrasion resistance.

3-2. Lambourn Abrasion Test

Comparative Examples 3-1 to 3-6

A Lambourn abrasion tester was used to measure the amount of abrasion at room temperature, a load of 1.0 kgf, and a slip ratio of 30%. The reciprocal of the determined amount of abrasion was expressed as an index, with the value of Comparative Example 3-1 as 100. A higher index value indicates higher abrasion resistance.

3-3. Abrasion Resistance Test on the Road

Test tires (tire size: 195/65R15) including tire tread portions formed from the compositions of Examples 3-1 to 3-6 and Comparative Examples 3-1 to 3-6 were each mounted on

TABLE 2

| | | Examples | | | | | | Comparative Examples | | | | | |
|---|---|---|---|---|---|---|---|---|---|---|---|---|---|
| | | 2-1 | 2-2 | 2-3 | 2-4 | 2-5 | 2-6 | 2-1 | 2-2 | 2-3 | 2-4 | 2-5 | 2-6 |
| Composition (part(s) by mass) | NR | 30 | 30 | 30 | 30 | 30 | 30 | 30 | 30 | 30 | 30 | 30 | 30 |
| | Polymer (1) | 70 | — | — | 70 | — | — | 70 | — | — | 70 | — | — |
| | Polymer (2) | — | 70 | — | — | 70 | — | — | 70 | — | — | 70 | — |
| | Polymer (3) | — | — | 70 | — | — | 70 | — | — | 70 | — | — | 70 |
| | Carbon black | 50 | 50 | 50 | — | — | — | 50 | 50 | 50 | — | — | — |
| | Aromatic oil | 20 | 20 | 20 | 20 | 20 | 20 | 20 | 20 | 20 | 20 | 20 | 20 |
| | Stearic acid | 2 | 2 | 2 | 2 | 2 | 2 | 2 | 2 | 2 | 2 | 2 | 2 |
| | Zinc oxide | 3 | 3 | 3 | 3 | 3 | 3 | 3 | 3 | 3 | 3 | 3 | 3 |
| | Antioxidant | 1 | 1 | 1 | 1 | 1 | 1 | 1 | 1 | 1 | 1 | 1 | 1 |
| | Wax | 1 | 1 | 1 | 1 | 1 | 1 | 1 | 1 | 1 | 1 | 1 | 1 |
| | Sulfur | 1.5 | 1.5 | 1.5 | 1.5 | 1.5 | 1.5 | 1.5 | 1.5 | 1.5 | 1.5 | 1.5 | 1.5 |
| | Vulcanization accelerator (1) | 1 | 1 | 1 | 1 | 1 | 1 | 1 | 1 | 1 | 1 | 1 | 1 |
| | Vulcanization accelerator (2) | 0.5 | 0.5 | 0.5 | 0.5 | 0.5 | 0.5 | 0.5 | 0.5 | 0.5 | 0.5 | 0.5 | 0.5 |
| Chipping resistance index | Small-angle scattering measurement method ($\Xi_c$) | 100 | 91 | 83 | 62 | 51 | 44 | — | — | — | — | — | — |
| | Chipping test on the road | — | — | — | — | — | — | 100 | 96 | 90 | 77 | 70 | 63 |

According to Table 2, the examples in which SANS measurement was used demonstrated that the chipping resistance can be evaluated by determining the correlation length $\Xi_c$ by curve fitting with equations 2-2 and 2-3. The measurement results of the examples were also highly correlated with the a Japanese FF (front-engine, front-wheel drive) car, and the groove depth in the tire tread portion of each tire after driving 8000 km was then measured. Based on the measured groove depth, the running distance corresponding to a 1 mm reduction in the groove depth of the tire was calculated, and then expressed as an index using the following equation, with the result of Comparative Example 3-1 as 100. A higher index value indicates better abrasion resistance.

(Index of abrasion resistance on the road)=(running distance corresponding to a 1 mm reduction in the groove depth)/(running distance corresponding to a 1 mm reduction in the groove depth of the tire of Comparative Example 1)×100 and q is defined by Equation 1-1:

$$q = \frac{4\pi \sin(\theta/2)}{\lambda}$$

TABLE 3

|  |  | Examples | | | | | | Comparative Examples | | | | | |
| --- | --- | --- | --- | --- | --- | --- | --- | --- | --- | --- | --- | --- | --- |
|  |  | 3-1 | 3-2 | 3-3 | 3-4 | 3-5 | 3-6 | 3-1 | 3-2 | 3-3 | 3-4 | 3-5 | 3-6 |
| Composition (part(s) by mass) | NR | 30 | 30 | 30 | 30 | 30 | 30 | 30 | 30 | 30 | 30 | 30 | 30 |
|  | Polymer (1) | 70 | — | — | 70 | — | — | 70 | — | — | 70 | — | — |
|  | Polymer (2) | — | 70 | — | — | 70 | — | — | 70 | — | — | 70 | — |
|  | Polymer (3) | — | — | 70 | — | — | 70 | — | — | 70 | — | — | 70 |
|  | Carbon black | 50 | 50 | 50 | — | — | — | 50 | 50 | 50 | — | — | — |
|  | Aromatic oil | 20 | 20 | 20 | 20 | 20 | 20 | 20 | 20 | 20 | 20 | 20 | 20 |
|  | Stearic acid | 2 | 2 | 2 | 2 | 2 | 2 | 2 | 2 | 2 | 2 | 2 | 2 |
|  | Zinc oxide | 3 | 3 | 3 | 3 | 3 | 3 | 3 | 3 | 3 | 3 | 3 | 3 |
|  | Antioxidant | 1 | 1 | 1 | 1 | 1 | 1 | 1 | 1 | 1 | 1 | 1 | 1 |
|  | Wax | 1 | 1 | 1 | 1 | 1 | 1 | 1 | 1 | 1 | 1 | 1 | 1 |
|  | Sulfur | 1.5 | 1.5 | 1.5 | 1.5 | 1.5 | 1.5 | 1.5 | 1.5 | 1.5 | 1.5 | 1.5 | 1.5 |
|  | Vulcanization accelerator (1) | 1 | 1 | 1 | 1 | 1 | 1 | 1 | 1 | 1 | 1 | 1 | 1 |
|  | Vulcanization accelerator (2) | 0.5 | 0.5 | 0.5 | 0.5 | 0.5 | 0.5 | 0.5 | 0.5 | 0.5 | 0.5 | 0.5 | 0.5 |
| Abrasion resistance index | Small-angle scattering measurement method (Nc) | 100 | 128 | 155 | 178 | 186 | 199 | — | — | — | — | — | — |
|  | Lambourn abrasion test | — | — | — | — | — | — | 100 | 100 | 101 | 122 | 123 | 123 |
|  | Abrasion resistance test on the road | 100 | 110 | 116 | 146 | 158 | 177 | 100 | 110 | 116 | 146 | 158 | 177 |

According to Table 3, the examples in which SANS measurement was used demonstrated that the abrasion resistance can be evaluated by determining the number $N_c$ of scatterers having the correlation length $\Xi_c$ per unit volume by curve fitting with equations 3-2 to 3-6. In particular, in comparison with the comparative examples, it is clear that the SANS measurement method provides highly accurate measurement of a small difference in abrasion resistance between samples, which is difficult to evaluate by a Lambourn abrasion test. It is also clear that the abrasion resistance can be successfully evaluated regardless of the presence or absence of carbon black.

The invention claimed is:

1. A method for evaluating energy loss in a polymeric material, comprising:

irradiating the polymeric material with X-rays or neutrons to perform X-ray scattering measurement or neutron scattering measurement, wherein the energy loss is evaluated based on a correlation length $\xi$ in a range of 1 nm to 100 μm determined by curve fitting equations 1-2 and 1-3 to a scattering intensity curve $I_{(q)}$ obtained by the X-ray scattering measurement or neutron scattering measurement:

$$I_{(q)} = \frac{A}{1+q^2\xi^2} + \frac{B}{(1+q^2\Xi_b^2)^2} + \frac{C}{(1+q^2\Xi_c^2)^2}, \quad \text{Equation 1-2}$$

and $$\xi < \Xi_b < \Xi_c \quad \text{Equation 1-3}$$

($A, B, C, \xi, \Xi_b, \Xi_c$: fitting parameters), wherein θ is the scattering angle and λ is the wavelength of X-rays or neutrons.

2. The method according to claim 1, wherein the X-ray scattering measurement is small-angle X-ray scattering measurement, and the neutron scattering measurement is small-angle neutron scattering measurement.

3. The method according to claim 1, wherein the polymeric material is a rubber material formed from at least one conjugated diene compound.

4. The method according to claim 3, wherein the rubber material is a rubber material for tires.

5. The method according to claim 1, wherein measurement is performed using the X-rays or neutrons under a condition where q defined by equation 1-1 is in a range of not more than 10 nm$^{-1}$.

6. A method for evaluating chipping resistance of a polymeric material, comprising:

irradiating the polymeric material with X-rays or neutrons to perform X-ray scattering measurement or neutron scattering measurement, wherein the chipping resistance is evaluated based on a correlation length $\Xi_c$ in a range of 1 nm to 100 μm determined by curve fitting equations 2-2 and 2-3 to a scattering intensity curve $I_{(q)}$ obtained by the X-ray scattering measurement or neutron scattering measurement:

$$I_{(q)} = \frac{A}{1+q^2\xi^2} + \frac{B}{(1+q^2\Xi_b^2)^2} + \frac{C}{(1+q^2\Xi_c^2)^2}, \quad \text{Equation 2-2}$$

and $$\xi < \Xi_b < \Xi_c \quad \text{Equation 2-3}$$

($A, B, C, \xi, \Xi_b, \Xi_c$: fitting parameters), and
q is defined by Equation 2-1:

$$q = \frac{4\pi \sin(\theta/2)}{\lambda}$$

wherein θ is the scattering angle and λ is the wavelength of X-rays or neutrons.

7. The method according to claim 6, wherein the X-ray scattering measurement is small-angle X-ray scattering measurement, and the neutron scattering measurement is small-angle neutron scattering measurement.

8. The method according to claim 6, wherein the polymeric material is a rubber material formed from at least one conjugated diene compound.

9. The method according to claim 8, wherein the rubber material is a rubber material for tires.

10. The method according to claim 6, wherein measurement is performed using the X-rays or neutrons under a condition where q defined by equation 2-1 is in a range of not more than 10 nm$^{-1}$.

11. A method for evaluating abrasion resistance of a polymeric material, comprising:
    irradiating the polymeric material with X-rays or neutrons to perform X-ray scattering measurement or neutron scattering measurement,
    wherein the abrasion resistance is evaluated based on a number $N_c$ per unit volume of scatterers having a correlation length $\Xi_c$ in a range of 1 nm to 100 μm determined by curve fitting equations 3-2 to 3-6 to a scattering intensity curve $I_{(q)}$ obtained by the X-ray scattering measurement or neutron scattering measurement:

$$I_{(q)} = \frac{A}{1+q^2\xi^2} + \frac{B}{(1+q^2\Xi_b^2)^2} + \frac{C}{(1+q^2\Xi_c^2)^2} \quad \text{Equation 3-2}$$

$$\xi < \Xi_b < \Xi_c, \quad \text{Equation 3-3:}$$

$$A = 8\pi N_a \sigma^2 \xi^3, \quad \text{Equation 3-4:}$$

$$B = 4\pi N_b \sigma^2 \Xi_b^2, \quad \text{Equation 3-5:}$$

$$C = 4\pi N_c \sigma^2 \Xi_c^2 \quad \text{Equation 3-6:}$$

(A, B, C, ξ, $\Xi_b$, $\Xi_c$: fitting parameters)
q is defined by Equation 3-1:

$$q = \frac{4\pi \sin(\theta/2)}{\lambda}$$

wherein θ is the scattering angle and λ is the wavelength of X-rays or neutrons,
$N_a$ is the number of scatterers having correlation length ξ per unit volume (N/cm$^3$),
$N_b$ is the number of scatterers having correlation length $\Xi_b$ per unit volume (N/cm$^3$),
$N_c$ is the number of scatterers having correlation length $\Xi_c$ per unit volume (N/cm$^3$), and
σ is the electron density difference (electron·cm$^{-3}$) between scatterer and surrounding matrix material, or scattering length density difference (cm$^{-2}$) between scatterer and surrounding deuterated solvent.

12. The method according to claim 11, wherein the X-ray scattering measurement is small-angle X-ray scattering measurement, and the neutron scattering measurement is small-angle neutron scattering measurement.

13. The method according to claim 11, wherein the polymeric material is a rubber material formed from at least one conjugated diene compound.

14. The method according to claim 13, wherein the rubber material is a rubber material for tires.

15. The method according to claim 11, wherein measurement is performed using the X-rays or neutrons under a condition where q defined by equation 3-1 is in a range of not more than 10 nm$^{-1}$.

* * * * *